(12) United States Patent
Morris et al.

(10) Patent No.: US 10,388,504 B2
(45) Date of Patent: *Aug. 20, 2019

(54) LOW CROSS-TALK FAST SAMPLE DELIVERY SYSTEM BASED UPON ACOUSTIC DROPLET EJECTION

(71) Applicant: Micromass UK Limited, Wilmslow, Cheshire (GB)

(72) Inventors: Michael Raymond Morris, Glossop (GB); Steven Derek Pringle, Darwen (GB); Keith Richardson, High Peak (GB); Ian Sinclair, Cheshire (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/982,451

(22) Filed: May 17, 2018

(65) Prior Publication Data
US 2018/0269051 A1    Sep. 20, 2018

Related U.S. Application Data

(63) Continuation of application No. 15/606,318, filed on May 26, 2017, which is a continuation of application No. 14/360,121, filed as application No. PCT/GB2012/052899 on Nov. 22, 2012, now Pat. No. 9,664,647.

(30) Foreign Application Priority Data

Nov. 22, 2011   (GB) .................................. 1120141.5

(51) Int. Cl.
*H01J 49/10*       (2006.01)
*H01J 49/04*       (2006.01)
*G01N 29/02*       (2006.01)
*H01J 49/00*       (2006.01)

(52) U.S. Cl.
CPC .............. *H01J 49/10* (2013.01); *G01N 29/02* (2013.01); *H01J 49/0027* (2013.01); *H01J 49/0454* (2013.01); *G01N 2291/011* (2013.01); *G01N 2291/02818* (2013.01)

(58) Field of Classification Search
USPC ........................................................ 250/282
See application file for complete search history.

(56) References Cited

U.S. PATENT DOCUMENTS

| 4,308,547 A | 12/1981 | Lovelady et al. |
| 4,815,323 A | 3/1989 | Ellinger et al. |
| 5,306,412 A | 4/1994 | Whitehouse et al. |

(Continued)

FOREIGN PATENT DOCUMENTS

WO     2010/118539 A2    10/2010

OTHER PUBLICATIONS

Extended European search report dated Nov. 6, 2017 for EP Application No. 17183141.5.

(Continued)

*Primary Examiner* — Phillip A Johnston
(74) *Attorney, Agent, or Firm* — Womble Bond Dickinson (US) LLP; Deborah M. Vernon; Heath T. Misley

(57) ABSTRACT

An ion source for a mass spectrometer is disclosed comprising an ultrasonic transducer which focuses ultrasonic energy onto a surface of a sample fluid without directly contacting the sample fluid.

20 Claims, 1 Drawing Sheet

(56) References Cited

U.S. PATENT DOCUMENTS

| | | | |
|---|---|---|---|
| 5,877,495 A | 3/1999 | Takada et al. | |
| 6,603,118 B2* | 8/2003 | Ellson | H01J 49/0454 |
| | | | 250/288 |
| 6,827,287 B2 | 12/2004 | Elrod et al. | |
| 7,185,969 B2* | 3/2007 | Mutz | B41J 2/04511 |
| | | | 347/20 |
| 7,208,727 B2 | 4/2007 | Fedorov et al. | |
| 7,399,497 B2 | 7/2008 | Imamura | |
| 7,915,579 B2 | 3/2011 | Chen et al. | |
| 8,153,964 B2 | 4/2012 | Chen et al. | |
| 8,641,971 B2 | 2/2014 | Van Doom et al. | |
| 9,664,647 B2* | 5/2017 | Morris | H01J 49/0454 |
| 2002/0109084 A1 | 8/2002 | Ellson et al. | |
| 2005/0054208 A1 | 3/2005 | Fedorov et al. | |
| 2007/0131871 A1 | 6/2007 | Chang et al. | |
| 2010/0078384 A1 | 4/2010 | Yang | |
| 2010/0301199 A1 | 12/2010 | Chen et al. | |

OTHER PUBLICATIONS

Elroad et al., "Nozzleless Droplet Formation with Focused Acoustic Beams", Journal of Applied Physics, vol. 65, No. 9, pp. 3441-3447 (1989).

Labcyte, "Acoustic Droplet Ejection 'Touchless' Transfer", Information/Reference No. 207HO, Labcyte Inc. 2007.

International Search Report and Written Opinion issued on Apr. 25, 2013 and dated May 7, 2013 for International Application No. PCT/GB2012/052899.

* cited by examiner

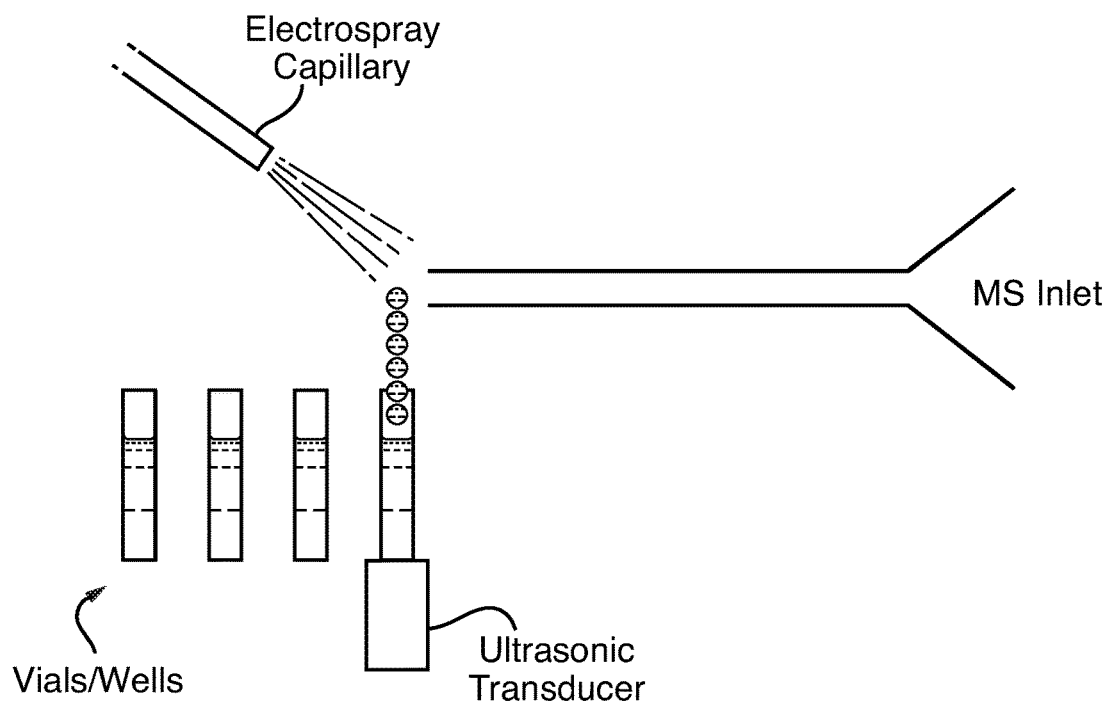

US 10,388,504 B2

LOW CROSS-TALK FAST SAMPLE DELIVERY SYSTEM BASED UPON ACOUSTIC DROPLET EJECTION

CROSS-REFERENCE TO RELATED APPLICATION APPLICATIONS

This Application is a Continuation of U.S. patent application Ser. No. 15/606,318 filed on May 26, 2017. U.S. patent application Ser. No. 15/606,318 is a Continuation of U.S. patent application Ser. No. 14/360,121 filed on May 22, 2014. U.S. patent application Ser. No. 14/360,121 claims priority from International Patent Application No. PCT/GB2012/052899 filed on Nov. 22, 2012 and claims priority from and the benefit of United Kingdom Patent Application No. 1120141.5 filed on 22 Nov. 2011. The entire contents of these applications are incorporated herein by reference in their entirety.

BACKGROUND TO THE PRESENT INVENTION

It is an increasingly common requirement of mass spectrometers to be able to rapidly process many samples. The sample may be a known substance and may have a known concentration. Alternatively, the sample may be unknown.

Injectors used in LC systems are known to be prone to sample contamination or cross-talk and a considerable amount of effort is expended during the design of these systems to seek to reduce the cross-talk or sample carry over that occurs in needle and sample transfer lines. Several "blank" or solvent injections are often required to be run in between injections to ensure that such systems are free of carry-over. This results in a reduction in the duty cycle of the system and less samples being analysed than could otherwise be possibly achievable.

It is desired to provide an improved ion source and method of ionising a sample.

SUMMARY OF THE PRESENT INVENTION

According to the present invention there is provided an ion source for a mass spectrometer comprising:

an ultrasonic transducer arranged and adapted to focus ultrasonic energy onto a surface of a sample fluid without the ultrasonic transducer directly contacting the sample fluid.

It is known to place fluid in direct contact with an inexpensive ultrasonic transducer which will result in an uncontrolled mist of droplets being formed. For example, it is known to use such devices to create a mist for air humidifiers. According to the present invention a more sophisticated and expensive ultrasonic transducer which is capable of focusing ultrasonic energy onto a surface of a fluid sample is utilised. It is not possible with a standard inexpensive transducer as used, for example, in an air humidifier to focus the ultrasonic energy. Importantly, the ultrasonic transducer according to the present invention does not directly contact the sample fluid. The sample fluid may, for example, be contained within a sample well of a microtitre plate and the ultrasonic transducer may be placed below the microtitre plate. According to the present invention ultrasonic energy is focused on to a surface of a sample fluid and this preferably causes one or more carefully controlled droplets to be ejected from the fluid sample in a precisely controlled manner. The droplets may, for example, have a volume of 2.5 nL and are preferably ejected individually and sequentially. The droplets are then preferably ionised by, for example, charged droplets emerging from an Electrospray ion source.

The present invention is particularly advantageous in that the means of ejecting droplets (i.e. the ultrasonic transducer) does not directly contact the fluid sample in contrast to e.g. LC injectors. As a result, the present invention solves the problem of cross talk which is common problem with e.g. injectors used in LC systems and other types of ion sources.

The present invention therefore enables droplets to be precisely and carefully ejected from e.g. different sample wells of a microtitre plate in a carefully controlled and rapid manner without the ion source suffering from the problem of cross contamination.

It is apparent, therefore, that the present invention is particularly advantageous.

According to the preferred embodiment the ultrasonic transducer is arranged and adapted to eject one or more droplets from the sample fluid in a substantially controlled manner.

The ultrasonic transducer is preferably arranged and adapted to eject multiple sequential individual droplets from the sample fluid in a substantially controlled manner.

The ultrasonic transducer is preferably arranged and adapted to eject one or more droplets from the sample fluid without forming an uncontrolled mist of droplets.

The ultrasonic transducer is preferably arranged and adapted to eject one or more droplets from the sample fluid wherein each droplet has a volume in the range: (i) <1 nL; (ii) 1-2 nL; (iii) 2-3 nL; (iv) 3-4 nL; (v) 4-5 nL; (vi) 5-6 nL; (vii) 6-7 nL; (viii) 7-8 nL; (ix) 8-9 nL; (x) 9-10 nL; (xi) 10-15 nL; (xii) 15-20 nL; (xiii) 20-25 nL; (xiv) 25-30 nL; and (xv) >30 nL. The ultrasonic transducer is preferably arranged and adapted to eject one droplet from the sample fluid every 1-100 µs, 100-200 µs, 200-300 µs, 300-400 µs, 400-500 µs, 500-600 µs, 600-700 µs, 700-800 µs, 800-900 µs, 900-1000 µs, 1-10 ms, 10-20 ms, 20-30 ms, 30-40 ms, 40-50 ms, 50-60 ms, 60-70 ms, 70-80 ms, 80-90 ms, 90-100 ms, 100-200 ms, 200-300 ms, 300-400 ms, 400-500 ms, 500-600 ms, 600-700 ms, 700-800 ms, 800-900 ms, 900-1000 ms or >1 s.

According to an embodiment the one or more droplets predominantly comprise ionised droplets. The one or more droplets are preferably ionised by charge segregation.

The sample fluid preferably comprises a polar sample, an ionic sample or a non-polar sample.

According to another embodiment the one or more droplets may comprise a majority of un-ionised droplets.

The ion source preferably further comprises an ionisation device. According to an embodiment the ionisation device comprises an Atmospheric Pressure Ionisation ("API") ionisation device. For example, according to an embodiment the Atmospheric Pressure Ionisation ionisation device may comprise an Electrospray ion source, an Atmospheric Pressure Chemical Ionisation ("APCI") ion source, an Impactor ion source wherein a sample is ionised upon impacting a target, a Laser ion source, an ultra-violet ("UV") photoionisation device or an infra-red ("IR") photoionisation device.

The ionisation device is preferably arranged and adapted to ionise the one or more droplets ejected from the sample fluid by the ultrasonic transducer.

The ionisation device is preferably arranged and adapted to act as a source of secondary ionisation for droplets ejected from the sample fluid by the ultrasonic transducer.

According to an embodiment the ultrasonic transducer is arranged and adapted to eject one or more droplets from the sample fluid into a stream of droplets or ions emitted by the ionisation device.

The ion source preferably further comprises a device arranged and adapted to position a sample well of a microtitre or multi-well sample plate adjacent the ultrasonic transducer.

In a mode of operation the ultrasonic transducer remains essentially static and the microtitre or multi-well sample plate is translated relative to the ultrasonic transducer.

In another embodiment the ion source comprises a device arranged and adapted to position the ultrasonic transducer adjacent a sample well of a microtitre or multi-well sample plate.

According to another embodiment in a mode of operation the microtitre or multi-well sample plate remains essentially static and the ultrasonic transducer is translated relative to the microtitre or multi-well sample plate.

The sample fluid is preferably contained, in use, within the sample well of the microtitre or multi-well sample plate.

The ultrasonic transducer is preferably arranged to make fluid contact with the microtitre or multi-well sample plate.

In a mode of operation one or more droplets are preferably sequentially ejected from different sample wells of the microtitre or multi-well sample plate.

The ultrasonic transducer is preferably arranged and adapted to detect and/or measure reflected ultrasonic energy (in contrast to basic inexpensive ultrasonic transducers as used, for example, in air humidifiers which have no capability to detect or measure reflected ultrasonic energy).

The ion source preferably further comprises a control system which is arranged and adapted to determine one or more first properties of the sample fluid.

According to an embodiment the control system is arranged and adapted to determine the surface height and/or surface position and/or density of the sample fluid.

The control system is preferably arranged and adapted to determine one or more first properties of the sample fluid using sonar.

The control system is preferably arranged and adapted to determine one or more first properties of the sample fluid by determining the time of flight and intensity or energy of a reflected sonar pulse.

According to an embodiment the sonar pulse has an energy in the range <100 mW, 100-200 mW, 200-300 mW, 300-400 mW or 400-500 mW and/or has a relative low energy so as not to cause ejection of droplets from the sample fluid.

The sonar pulse preferably reflects, in use, from a surface of the sample fluid.

The control system is preferably arranged and adapted to control the focusing of the ultrasonic energy onto the surface of the sample fluid based upon the determined one or more first properties of the sample fluid.

The ultrasonic transducer is preferably arranged to emit ultrasonic waves having a frequency in the range: (i) 20-30 kHz; (ii) 30-40 kHz; (iii) 40-50 kHz; (iv) 50-60 kHz; (v) 60-70 kHz; (vi) 70-80 kHz; (vii) 80-90 kHz; (viii) 90-100 kHz; and (ix) >100 kHz.

According to another aspect of the present invention there is provided a mass spectrometer comprising an ion source as described above.

The mass spectrometer preferably comprises an ion inlet. The ion inlet preferably leads from a substantially atmospheric pressure region to a substantially sub-atmospheric pressure region.

The ultrasonic transducer is preferably arranged and adapted to eject one or more droplets adjacent the ion inlet so that resulting analyte molecules and/or ions enter the mass spectrometer via the ion inlet.

The mass spectrometer preferably further comprises a gas phase ion mobility spectrometer or separator, wherein the ion mobility spectrometer or separator is arranged and adapted to separate analyte ions temporally according to their ion mobility.

According to another aspect of the present invention there is provided a method of ionising a sample comprising:

focusing ultrasonic energy onto a surface of a sample fluid without directly contacting the sample fluid.

The method preferably further comprises ionising droplets ejected from the sample fluid using an Atmospheric Pressure Ionisation ("API") device.

According to another aspect of the present invention there is provided a method of mass spectrometry comprising a method of ionising a sample as described above.

According to another aspect of the present invention there is provided an ion source for a mass spectrometer comprising:

an ultrasonic transducer arranged and adapted to focus ultrasonic energy onto a surface of a sample fluid contained, in use, within a sample well without the ultrasonic transducer directly contacting the sample fluid so as to eject one or more droplets from the sample fluid in a controlled manner without forming an uncontrolled mist of droplets; and an ionisation device arranged and adapted to ionise the one or more droplets.

According to another aspect of the present invention there is provided a method of ionising a sample comprising:

providing an ultrasonic transducer and focusing ultrasonic energy onto a surface of a sample fluid contained within a sample well without the ultrasonic transducer directly contacting the sample fluid so as to eject one or more droplets from the sample fluid in a controlled manner without forming an uncontrolled mist of droplets; and ionising the one or more droplets.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; and (xxi) an Impactor ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wein filter; and/or (k) a device or ion gate for pulsing ions; and/or (l) a device for converting a substantially continuous ion beam into a pulsed ion beam.

The mass spectrometer may further comprise either:

(i) a C-trap and an Orbitrap® mass analyser comprising an outer barrel-like electrode and a coaxial inner spindle-like electrode, wherein in a first mode of operation ions are transmitted to the C-trap and are then injected into the Orbitrap® mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the Orbitrap® mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

BRIEF DESCRIPTION OF THE DRAWINGS

Various embodiments of the present invention will now be described, by way of example only, and with reference to the accompanying drawing in which:

FIG. 1 shows a preferred embodiment of the present invention wherein an ultrasonic transducer sequentially emits droplets from a well of a microtitre plate and wherein the droplets are ionised by ionised droplets emitted from an Electrospray ion source.

DETAILED DESCRIPTION OF PREFERRED EMBODIMENT

A preferred embodiment of the present invention will now be described with reference to FIG. 1.

FIG. 1 shows a preferred embodiment of the present invention wherein an ultrasonic transducer is arranged so as to sequentially emit single droplets from a well of a microtitre plate and wherein the droplets are subsequently ionised by ionised droplets emitted from an Electrospray ion source.

According to the preferred embodiment an acoustic droplet ejection technique is used as a liquid transfer process that allows both volumetric and positional control of liquid droplets without the requirement for needles or nozzles. The technique focuses ultrasonic energy onto a fluid surface causing a small droplet to be ejected. Droplets with a volume as low as 1 pL and as high as 10 mL may be ejected. The system can be configured to eject droplets in sequence allowing larger volumes of liquid to be ejected from the surface. Advantageously, the method of ejecting droplets which are preferably ionised by an Electrospray or other atmospheric pressure ion source does not require disposable tips or nozzles. A yet further advantage is that there is no requirement to wash and clean the transfer mechanism thereby saving both time and cost.

It will be apparent to a person skilled in the art that the approach of dispensing individual droplets in a controlled manner whilst eliminating the chance of cross-contamination has particular utility with biological samples dispensed in multiple different wells of e.g. a microtitre plate.

According to an embodiment of the present invention ultrasonic energy or sound waves are transmitted by an ultrasonic transducer through the base of a sample well and through a fluid located within the sample well. The pressure of the ultrasonic energy or wave is preferably focussed at the surface of the sample fluid and causes a droplet of fluid to be ejected from the sample fluid in a carefully controlled manner.

The ultrasonic transducer is preferably kept in a fixed relationship with an ion inlet into a vacuum chamber of a mass spectrometer and a microtitre plate is preferably translated so as to bring different sample wells in the microtitre plate into contact with the ultrasonic transducer. The ultrasonic transducer preferably makes fluid contact with the underside of the microtitre plate in order to ensure a controlled transmission of sound energy into and through the sample well.

According to a preferred embodiment the non-contact and accurate volumetric droplet delivery system is preferably coupled with a secondary ionisation mechanism (e.g. Extractive Electrospray) and a mass spectrometer to produce a fast, low cross-contamination sample delivery system.

According to an embodiment droplets may be ejected by the ultrasonic transducer into an ultrasonic trap. The droplets may then be trapped and/or levitated and a field may be applied in order to ionise the droplets by a process known as Field Induced Droplet Ionization ("FIDI"). This allows direct Electrospray from the droplets without the need for additional solvent.

In order to locate the surface of the sample fluid a low energy sonar pulse is preferably directed into the sample fluid in order to determine the density and the depth of the sample fluid. A portion of the sonar pulse is reflected back from each interface encountered by the sonar pulse. For example, a first echo is reflected from the bottom surface of the microtitre plate and another second echo is received from the inside bottom of a well of the microtitre plate. A further third echo is received from the surface of the liquid which forms a liquid:air interface. The ratio of the energy of the first and second echoes is used to determine the acoustic impedance of the fluid which enables the speed of sound in the liquid to be determined. This in turn enables the depth of the sample fluid to be determined by measuring the time taken for sound to be reflected from the liquid:air interface. The ultrasonic transducer can then be arranged so as to focus ultrasonic or acoustic energy onto a surface of the sample fluid in an optimal manner.

Although the present invention has been described with reference to preferred embodiments, it will be understood by those skilled in the art that various changes in form and detail may be made without departing from the scope of the invention as set forth in the accompanying claims.

The invention claimed is:

1. An ion source for a mass spectrometer comprising:
   a transducer arranged and adapted to focus acoustic energy onto a surface of a sample fluid without said transducer directly contacting said sample fluid, wherein said transducer is arranged and adapted to eject one or more droplets from said sample fluid in a substantially controlled manner; and
   an ionisation device arranged and adapted to ionise a volume of liquid comprising said one or more droplets ejected from said sample fluid by said transducer, wherein said ionisation device is arranged and adapted to emit a stream of charged particles that is separate from said one or more droplets ejected from said sample fluid by said transducer.

2. An ion source as claimed in claim 1, wherein said transducer is arranged and adapted to eject multiple sequential individual droplets from said sample fluid in a substantially controlled manner.

3. An ion source as claimed in claim 1, wherein said transducer is arranged and adapted to eject one or more droplets from said sample fluid without forming an uncontrolled mist of droplets.

4. An ion source as claimed in claim 1, wherein said one or more droplets comprise a majority of un-ionised droplets.

5. An ion source as claimed in claim 1, wherein said sample fluid comprises a polar sample, an ionic sample or a non-polar sample.

6. An ion source as claimed in claim 1, wherein said ionisation device comprises an Atmospheric Pressure Ionisation ("API") ionisation device.

7. An ion source as claimed in claim 1, wherein said ionisation device comprises an Electrospray ion source, an Atmospheric Pressure Chemical Ionisation ("APCI") ion source, an Impactor ion source wherein a sample is ionised upon impacting a target, a Laser ion source, an ultra-violet ("UV") photoionisation device or an infra-red ("IR") photoionisation device.

8. An ion source as claimed in claim 1, wherein said ionisation device is arranged and adapted to act as a source of secondary ionisation for said volume of liquid comprising said one or more droplets ejected from said sample fluid by said transducer.

9. An ion source as claimed in claim 1, wherein said separate stream of charged particles emitted by said ionisation device comprise charged droplets or ions.

10. An ion source as claimed in claim 1, further comprising a device arranged and adapted to position a sample well of a microtitre or multi-well sample plate adjacent said transducer or a device arranged and adapted to position said transducer adjacent a sample well of a microtitre or multi-well sample plate.

11. An ion source as claimed in claim 9, wherein said sample fluid is contained, in use, within said sample well of said microtitre or multi-well sample plate.

12. An ion source as claimed in claim 9, wherein said transducer is arranged to make fluid contact with said microtitre or multi-well sample plate.

13. An ion source as claimed in claim 9, wherein in a mode of operation one or more droplets are sequentially ejected from different sample wells of said microtitre or multi-well sample plate.

14. A mass spectrometer comprising an ion source as claimed in claim 1.

15. A mass spectrometer as claimed in claim 13, wherein said mass spectrometer comprises an ion inlet.

16. A mass spectrometer as claimed in claim 15, wherein said ion inlet leads from a substantially atmospheric pressure region to a substantially sub-atmospheric pressure region.

17. A mass spectrometer as claimed in claim 15, wherein said ion source is adjacent said ion inlet so that resulting analyte molecules and/or ions enter said mass spectrometer via said ion inlet.

18. A mass spectrometer as claimed in claim 14, further comprising a gas phase ion mobility spectrometer or separator, wherein said ion mobility spectrometer or separator is arranged and adapted to separate analyte ions temporally according to their ion mobility.

19. A method of ionising a sample comprising:
focusing acoustic energy onto a surface of a sample fluid using a transducer without said transducer directly contacting said sample fluid; and
ionising a volume of liquid comprising said one or more droplets ejected from said sample fluid by said transducer using an ionisation device, wherein said ionisation device is arranged and adapted to emit a stream of charged particles that is separate from said one or more droplets ejected from said sample fluid by said transducer.

20. A method of mass spectrometry comprising a method of ionising a sample as claimed in claim 19.

* * * * *